United States Patent [19]

Anderson

[11] 4,133,842
[45] Jan. 9, 1979

[54] PRODUCTION AND RECOVERY OF LINEAR MONO-OLEFINS

[75] Inventor: Mark C. Anderson, Palatine, Ill.

[73] Assignee: UOP Inc., Des Plaines, Ill.

[21] Appl. No.: 844,676

[22] Filed: Oct. 25, 1977

[51] Int. Cl.² .............................................. C07C 5/32
[52] U.S. Cl. .................................. 260/683.3; 208/49; 208/62; 208/99
[58] Field of Search ................. 260/683.3; 208/49, 62, 208/99

[56] References Cited

U.S. PATENT DOCUMENTS

| 3,201,344 | 8/1965 | Broughton | 208/143 |
|---|---|---|---|
| 3,239,455 | 3/1966 | Lickus et al. | 208/212 |
| 3,293,319 | 12/1966 | Haensel et al. | 260/683.3 |
| 3,360,586 | 12/1967 | Bloch et al. | 260/683.3 |
| 3,448,165 | 6/1969 | Bloch | 260/683.3 |
| 3,510,423 | 5/1970 | Neuzil et al. | 208/310 |
| 3,542,667 | 11/1970 | McMahon et al. | 208/62 |
| 3,617,504 | 11/1971 | Berg | 260/683.3 |
| 3,649,176 | 3/1972 | Rosback | 252/455 |
| 3,718,580 | 2/1973 | Rosback | 260/677A |
| 3,917,540 | 11/1975 | Pollitzer | 208/138 |

*Primary Examiner*—Veronica O'Keefe
*Attorney, Agent, or Firm*—James R. Hoatson, Jr.; Robert W. Erickson; William H. Page, II

[57] ABSTRACT

Normal paraffinic hydrocarbons, having from three to about twenty carbon atoms per molecule, are dehydrogenated to produce corresponding linear mono-olefins.-These are separated from unreacted paraffins, preferably via an adsorption-separation technique. Raffinate, containing the unreacted normal paraffins, is subjected to mild hydrotreating, as is the hydrogen-rich vaporous phase recovered from the dehydrogenation zone product effluent, to saturate the olefins therein. Hydrotreated effluent is introduced, generally in admixture with fresh feed paraffins, into the dehydrogenation reaction zone.-This technique avoids by-product dehydrogenation reactions otherwise resulting in non-linear mono-olefins, di-olefinic hydrocarbons and aromatics.

10 Claims, 1 Drawing Figure

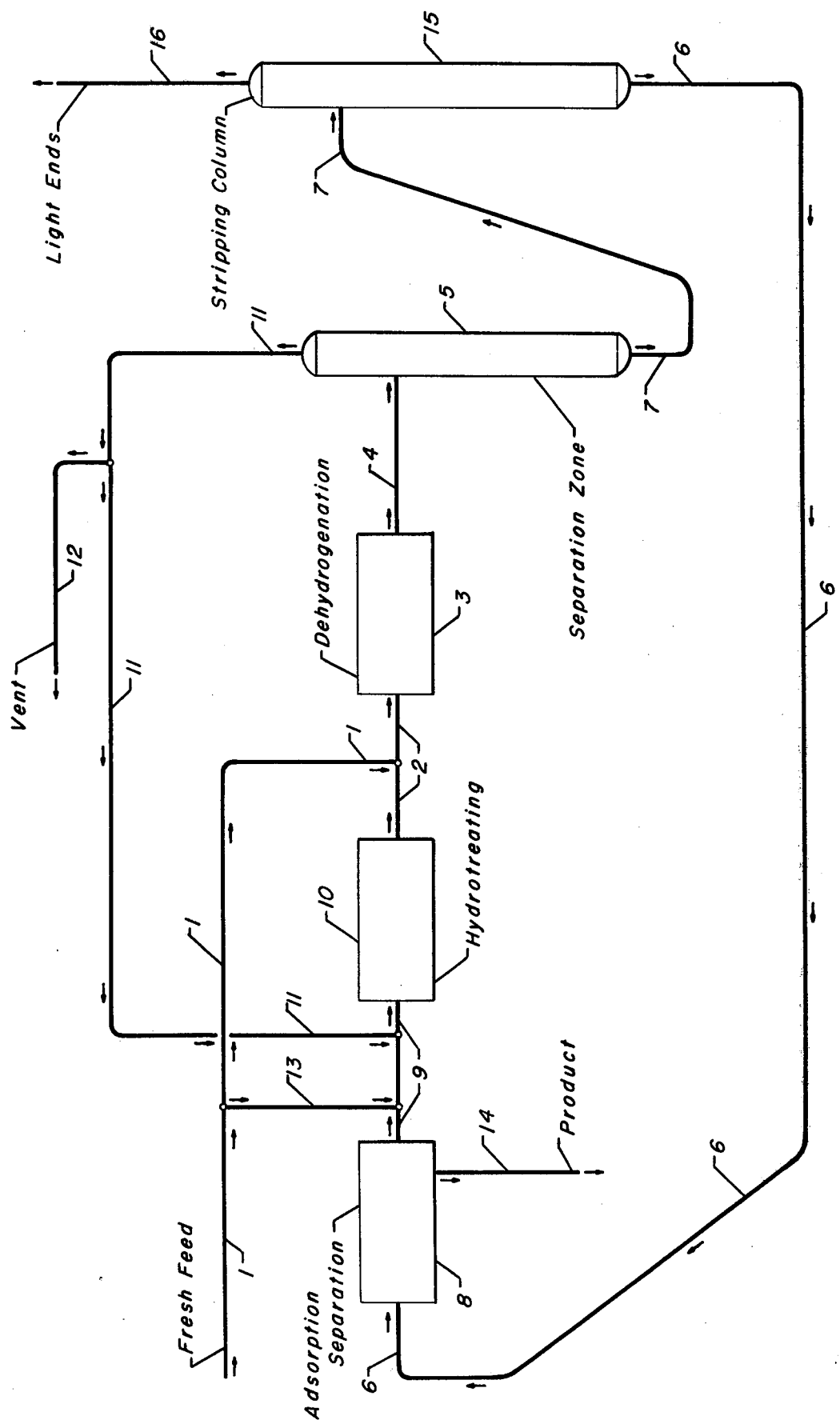

PRODUCTION AND RECOVERY OF LINEAR MONO-OLEFINS

APPLICABILITY OF INVENTION

Although the process encompassed by the inventive concept herein described may be suitably utilized to improve the dehydrogenation of normal paraffins having from three to about twenty carbon atoms per molecule, it is more particularly directed toward the production of linear mono-olefins from paraffinic hydrocarbons containing about six to about eighteen carbon atoms per molecule. Longer-chain paraffins, having from about eleven to eighteen carbon atoms per molecule, are more advantageously dehydrogenated to the corresponding linear mono-olefins which are intended for utilization in the manufacture of biodegradable detergents. Other uses for olefinic hydrocarbons are numerous throughout the petroleum and petrochemical industries. For example, propylene is widely employed in the manufacture of isopropyl alcohol, propylene dimer, trimer and tetramer, cumene, polypropylene, and in isoprene synthesis. Butene enjoys extensive use in polymer and alkylate gasolines, in the manufacture of polybutenes, butadiene, aldehydes, alcohols and as cross-linking agents for polymers. Pentenes are primarily utilized in organic synthesis, or as a blending agent for high octane gasolines. Olefins having six to ten carbon atoms find widespread use in the preparation of flavors, dyes, resins, plasticizers and medicines, and in organic synthesis. These uses of olefins, particularly those intended for detergent manufacture, generally require substantially pure linear mono-olefinic feedstocks virtually void of di-olefins, non-linear mono-olefins and aromatics.

The charge stock to the present process is a substantially pure normal paraffin concentrate; the particular source thereof is not considered to be a feature which is limiting upon the present invention. Within the range of about three to 20 carbon atoms per molecule, the fresh feed may be selectively concentrated in a single species — e.g. normal heptane — or, in two or more, such as hexane, heptane and octane. Since biodegradable detergents are preferentially prepared from relatively long-chain mono-olefins, a preferred charge stock constitutes normal paraffins having from about eleven to about eighteen carbon atoms per molecule.

The lower molecular weight paraffins, propane and butane, are found in abundance in off-gases from various petroleum refining operations; although they have other uses, such off-gas streams are suitable feedstocks to the present combination process. Normally liquid hydrocarbons, having five to nine carbon atoms per molecule, can be obtained from straight-run, or catalytically-cracked naphtha fractions. Kerosene and gas oil boiling range distillates constitute a suitable source of those paraffinic hydrocarbons having ten to about twenty carbon atoms per molecule. In view of the fact that the charge stock is a substantially pure normal paraffinic concentrate, non-normals are generally removed from the foregoing proposed feed streams; this may be accomplished by way of an adsorption-separation process utilizing a zeolitic molecular sieve which selectively adsorbs the normal paraffins, while simultaneously rejecting the isomeric counterparts thereof. It is understood that neither the particular charge stock, nor the precise source thereof is limiting upon the scope of the present invention.

Briefly, the normal paraffin concentrate is reacted in a catalytic dehydrogenation reaction zone, in a hydrogen atmosphere, at operating conditions selected to produce linear mono-olefinic counterparts. The product effluent is separated, generally in a high-pressure separation zone, to provide (1) a normally liquid hydrocarbon phase containing mono-olefinic hydrocarbons and unreacted feed stream normal paraffins, and, (2) a hydrogen-rich, principally vaporous phase. The former stream is separated, preferably in a molecular sieve adsorption-separation zone hereafter described in detail, to recover the desired mono-olefinic product and to provide a recycle stream of unreacted normal paraffins. Heretofore, the vaporous phase, after venting of a portion to remove excess hydrogen from the system, has been directly recycled to the dehydrogenation zone. Since this vaporous phase contains olefins, some of which have the same number of carbon atoms per molecule as the feed stream normal paraffins, the charge to the dehydrogenation zone is contaminated and the effluent therefrom will contain, therefore, undesirable non-linear olefins, aromatics and di-olefins. In accordance with the present invention, the vaporous phase is introduced into a mild hydrotreating catalytic reaction zone in which such olefins are saturated and thereby rendered innocuous. Likewise, the unreacted normal paraffinic concentrate, intended for recycle to the dehydrogenation reaction zone, will contain minor amounts of olefinic material; it is, therefore, also first introduced into the hydrotreating zone. Hydrotreating is effected at mild operating conditions which will not induce cracking reactions resulting in degradation of the paraffinic components in the feed stream.

OBJECTS AND EMBODIMENTS

A principal object of my invention is to provide a more efficient and economical process for the production and recovery of linear mono-olefins. A corollary objective is to enhance the efficiency of a catalytic dehydrogenation reaction zone.

More specifically, it is an object to improve the quantity of the linear mono-olefinic product emanating from a dehydrogenation reaction zone through a technique which decreases the quantity of di-olefins, aromatics and non-linear olefins contained therein.

Therefore, in one embodiment, my invention is directed toward a process for dehydrogenating a hydrocarbon charge stock, containing normal paraffins having from about 3 to about 20 carbon atoms per molecule, which comprises the steps of: (a) reacting said charge stock and hydrogen, in a dehydrogenation reaction zone, at dehydrogenation conditions selected to convert paraffinic hydrocarbons to mono-olefinic hydrocarbons; (b) separating the resulting dehydrogenation zone effluent, in a first separation zone, at separating conditions to provide (1) a hydrogen-rich, principally vaporous phase containing olefinic hydrocarbons and, (2) a second phase containing mono-olefinic hydrocarbons and unreacted normal paraffins; (c) separating said second phase, in a second separation zone to (1) recover said mono-olefinic hydrocarbons and, (2) provide a normal paraffin concentrate containing olefinic hydrocarbons; (d) reacting at least a portion of said hydrogen-rich vaporous phase, in a hydrotreating zone, at hydrotreating conditions selected to saturate the olefinic hydrocarbons therein; and, (e) introducing the resulting substantially olefin-free effluent from said hydrotreating reaction zone into said dehydrogenation reaction zone.

This embodiment is further characterized in that said normal paraffin concentrate, containing olefinic hydrocarbons is introduced into said hydrotreating reaction zone. Various other objects and embodiments will become evident, to those possessing the requisite degree of skill in the appropriate art, from the following more detailed discussion. In one such other embodiment, the second separation zone is an adsorption-separation zone having disposed therein a zeolitic crystalline aluminosilicate molecular sieve.

CITATION OF RELEVANT PRIOR ART

As above set forth, the present combination is founded upon recognition of the fact that the hydrogen-rich recycled vaporous phase to a catalytic dehydrogenation reaction zone contains sufficient olefinic hydrocarbons, in the feed stream carbon number range, to adversely affect the quality of the desired linear mono-olefinic product effluent. Thus, in accordance with my invention, the recycled vaporous phase is subjected to a mild hydrotreating step for olefin saturation to produce additional feed stream normal paraffins. Additionally, since the separation of the dehydrogenation reaction zone effluent results in an unreacted paraffin concentrate containing product olefins, the unreacted paraffins are also subjected to mild hydrotreating prior to being recycled to the dehydrogenation zone.

It is recognized and acknowledged that many illustrations of catalytic dehydrogenation processing techniques are to be found in the prior art; likewise, hydrotreating processes for olefin saturation, as well as removal of contaminating influences (mainly sulfur and nitrogen removal), are well known and thoroughly described. Thus, relevant prior art will be directed toward combinations of hydrotreating and catalytic dehydrogenation. In a like vein, the intended mono-olefinic product is preferably separated from the mixture thereof with unreacted normal paraffins via molecular sieve adsorption; therefore, additional relevant prior art involves the combination of such adsorption-separation with (1) dehydrogenation and, (2) hydrotreating and dehydrogenation. Copies of the prior art hereinbelow delineated accompany this application.

Considering first the dehydrogenation reaction, U.S. Pat. No. 3,293,319 (Cl. 260–683.3), issued Dec. 26, 1966, is principally directed toward the production of mono-olefins from paraffins containing three or more carbon atoms per molecule, specifically those having a carbon number of six or more. The viability of the invention appears to involve the addition of arsenic, antimony and/or bismuth to a catalytic composite of alumina, lithium and a Group VIII metallic component, particularly a noble metal such as platinum. The addition of the metallic attenuator from Group V-A inhibits isomerization and/or cracking reactions. U.S. Pat. No. 3,360,586 (Cl. 260-683.3), issued Dec. 26, 1967, is similar except that the liquid hourly space velocity is increased to a range of from 12.0 to about 40.0 and the reactions are effected in the presence of at least 400 ppm. by weight of added water. In both the described techniques, reaction zones pressure is maintained via compressive hydrogen recycle; however, there is no recognition of the recycle hydrogen containing olefinic hydrocarbons and no awareness of the necessity to hydrogenate the same prior to the introduction thereof into the dehydrogenation reaction zone. U.S. Pat. Nos. 3,448,165 (Cl. 260-683.3), issued June 3, 1969, and 3,917,540 (Cl. 252-466PT), issued Nov. 4, 1975, are cumulative to the foregoing with the exception that the latter is specifically directed toward a dehydrogenation catalytic composite which incorporates a Group VII-B metallic component.

Liquid-phase adsorption-separation of normal olefins, having from about ten to about 20 carbon atoms per molecule, from a mixture thereof with normal paraffins, is the principal subject of U.S. Pat. No. 3,510,423 (Cl. 208-310), issued May 5, 1970. The adsorbent is a type X or type Y zeolite containing at least one cation selected from the metals of Groups I-A, I-B, II-A and II-B. Operating conditions imposed upon the adsorption column include a temperature in the range of 25° C. to about 150° C. and a pressure of from atmospheric to about 500 psig. In Column 8, Line 22 through Column 9, Line 17, there is disclosed the use of normally liquid dehydrogenation zone effluent as the charge to the adsorption column. The disposition of the remainder of the dehydrogenation reaction product effluent is not discussed; there is, therefore no recognition that the same is at least in part hydrotreated and recycled to the reaction zone. Additionally, there is no awareness of passing the normal paraffinic raffinate to the dehydrogenation zone, nor of hydrotreating the same before so doing.

U.S. Pat. No. 3,649,176 (Cl. 23-111), issued Mar. 14, 1972, is directed toward a method for the preparation of a copper-exchanged type X zeolitic material. It is intended that this adsorbent be utilized in the separation of mono-olefins, having from 10 to about 20 carbon atoms per molecule, from normal paraffins. The process is the subject of U.S. Pat. No. 3,718,580 (Cl. 208-310), issued Feb. 27, 1973. As a practical consideration, these references appear to be cumulative to U.S. Pat. No. 3,510,423, above discussed.

U.S. Pat. No. 3,617,504 (Cl. 208-100), issued Nov. 2, 1971, specifically discloses a combination of (1) dehydrogenation of normal paraffins in the 6 to 20 carbon number range, (2) recycle of a portion of the hydrogen-rich vaporous phase separated from the dehydrogenation zone effluent, (3) adsorption-separation of the desired mono-olefins from unreacted paraffins and, (4) recycle of the normal paraffinic raffinate to the dehydrogenation reaction zone. This particular combination is illustrated clearly in FIG. 1. The separated hydrogen-rich vaporous phase from separation zone 12 passes directly, via line 3, into the dehydrogenation zone 11. Likewise, the normal paraffinic raffinate stream from adsorption-separation zone 14 is recycled, via line 10, to combine with the fresh feed to the dehydrogenation reaction zone. Noteworthy is the fact that these streams are returned to the dehydrogenation zone without the benefit of intermediate catalytic hydrotreating for olefin saturation. Therefore, there exists no cognizance of the presence of olefinic material, having feed stream carbon numbers, in either the hydrogen recycle, or the paraffinic raffinate recycle.

It is, however, recognized at Column 2, Line 55 through Column 3, Line 22, that aromatics can be removed from the paraffin recycle either via acid treating, or the removal of a so-called drag stream. Nothing is therein stated regarding the return of olefinic hydrocarbons to the dehydrogenation reaction zone.

U.S. Pat. No. 3,201,344 (Cl. 208-143), issued Aug. 17, 1965, is specifically directed toward a combination process involving hydrogenation and adsorption-separation for refining hydrocarbon lubricating oils. Adsorption-separation is effected utilizing a 13× or 10× molecular sieve to reject, as the raffinate stream, branched chain hydrocarbons, polynuclear cyclics and polyalkyl-substituted cyclics which are the less desirable components of lubricating oils. Prior to adsorptive separation, the lube oil stock is subjected to hydrogenation to saturate the aromatic and olefinic hydrocarbons (Column 4, Lines 14–30) to provide the more desirable paraffinic and naphthenic components of the lubricating oil. The hydrogenative pretreatment is apparently conducted in a liquid-phase operation (Column 7, Lines 17–49).

U.S. Pat. No. 3,239,455 (Cl. 208-212), issued Mar. 8, 1966, is primarily concerned with the recovery of normal aliphatic hydrocarbons boiling in the kerosene boiling range for ultimate use in detergent manufacture (Column 1, Lines 14–45). Hydrogenation of the fresh feed charge stock is effected to eliminate nitrogenous and sulfurous compounds, and to saturate olefinic and aromatic hydrocarbons (Column 2, Lines 1–45). The hydrogenation pretreatment is effected in liquid phase (Column 6, Lines 43–54 and Column 12, Lines 20–25).

In these last-mentioned prior art references, the hydrotreating is effected to reduce the aromatic and olefinic content of the charge to the zeolitic adsorption-separation zone which recovers normal paraffins (extract) from isoparaffins (raffinate). Hydrotreating the charge to the adsorption-separation zone of the present process would destroy entirely its intended function of recovering mono-olefins (extract) from a mixture thereof with normal paraffins (raffinate).

SUMMARY OF INVENTION

As hereinbefore set forth, the combination process encompassed by my inventive concept is intended to be applied to the production and recovery of linear mono-olefins. Production is effected by way of dehydrogenating normal paraffins of the same carbon number as the desired mono-olefin; recovery of the product is effected utilizing crystalline aluminosilicate adsorption-separation wherein the selected molecular sieve adsorbent retains the olefins (extract) and rejects unreacted normal paraffins (raffinate). As above indicated, and in contrast to the prior art delineated, either the unreacted paraffinic raffinate, or the hydrogen-rich vaporous phase separated from the dehydrogenated product effluent may be hydrotreated before being recycled to the dehydrogenation reaction zone. Olefinic material contained in these recycled streams will dehydrogenate to form di-olefins, or otherwise convert to non-normal olefins and aromatics in the dehydrogenation zone. These will ultimately appear in the extract phase desorbed from the zeolitic material in the adsorption-separation zone, and detrimentally affect the ultimate intended use of the mono-olefinic product.

Hydrotreating is effected intermediate the adsorption-separation zone and the catalytic dehydrogenation reaction zone, and at mild operating conditions which will saturate olefinic hydrocarbons without inducing cracking reactions. Briefly, fresh feed normal paraffins, having the desired carbon number range, and make-up hydrogen (compensating for that removed as a vented drag stream and consumed in olefin saturation) is introduced into the dehydrogenation reaction zone. The product effluent is separated, generally in a high-pressure phase-separation zone to provide a hydrogen-rich vaporous phase and a mono-olefinic phase which contains unreacted normal paraffins. A portion of the former is vented from the process, generally on pressure control, and the remainder is introduced into the hydrotreating zone. The mono-olefinic/normal paraffin mixture is introduced into the adsorption-separation zone, contacting therein a crystalline aluminosilicate from the group of type X and type Y zeolites. Mono-olefins are selectively retained within these molecular sieves, and removed and recovered therefrom through the use of a suitable desorbent.

A normal paraffin concentrate, rejected by the zeolitic adsorbent, withdrawn as a raffinate stream containing a minor quantity of mono-olefins, is introduced into the hydrotreating zone, preferably in admixture with the hydrogen-rich recycled stream. Olefin saturation may be carried out in either vapor phase, or in liquid phase (discounting the hydrogen), the selected technique generally depending upon the carbon number, or range thereof, of the charge thereto. Hydrotreating conditions are selected to preclude the possibility of cracking reactions taking place, and include temperatures in the range of about 100° F. to about 600° F., preferably 200° F. to 500° F. The hydrotreating reaction zone will be maintained at a pressure of about 50 to about 500 psig., and preferably from about 50 to about 400 psig. Mild hydrotreating conditions afford comparatively high space velocities in the range of about 3.0 to about 10.0 and relatively low hydrogen to hydrocarbon mole ratios from about 1.0 to about 5.0.

The substantially non-acidic (low activity relative to cracking functions) catalytic composite, disposed in the hydrotreating zone, contains at least one Group VIII noble metal component in the amount of about 0.1% to about 1.5% by weight, calculated as the elemental metal. Suitable noble metal components are ruthenium, osmium, rhodium, iridium, platinum, palladium and various mixtures thereof. Preferably, these are composited with an alumina carrier material. The use of the term "non-acidic" is intended to connote that intentional steps to provide an acid function — e.g. incorporation of silica or a halogen component — in the catalyst are not taken. Noble metals, especially platinum and palladium, as well as the alumina carrier material, possess sufficient natural acidity to effect olefin saturation at a low-severity operation. The thus-hydrotreated hydrogen-rich recycled vaporous phase and normal paraffinic raffinate are admixed with fresh paraffinic charge stock and introduced therewith into the dehydrogenation zone.

NORMAL PARAFFIN DEHYDROGENATION

Dehydrogenation of the normal paraffinic hydrocarbons is effected in the presence of hydrogen and in contact with a catalytic composite substantially void of acid-acting activity. The catalyst, as well as the various operating-variable ranges, are intentionally selected to preclude any significant degree of undesirable side reactions. This is, of course, recognized in the dehydrogenation prior art hereinbefore specifically delineated. The disclosed catalysts and operating conditions are suitable also for utilization in the present combination process. Selections of specific catalytic composites and operating variables will depend upon the precise character of the normal paraffin feedstock with respect to carbon number; that is, the selection may well vary for a charge having 3 to 5 carbon atoms per molecule from a feed stream having 11 to 18 carbon atoms per molecule. Catalytic composites having at least one Group VIII nobel metal component and at least one alkalinous metal component, composited with an alumina carrier material, are preferred. These may also contain one or more of the attenuators — arsenic, antimony, bismuth — described in the prior art. Furthermore, dehydrogenation catalysts may have one or more catalytic modifiers incorporated therein; these would include metals such as rhenium, tin, germanium, cobalt, vanadium and nickel.

Dehydrogenation will generally prove beneficial when effected at a temperature in the range of about 750° F. to about 1050° F., although the intermediate range of about 800° F. to about 950° F. is preferred. Operating pressure is relatively low, compared to other petroleum refining processes, and will be from about 10 psig. to about 100 psig.; in most applications, reaction zone pressure will be at least 15 psig., but not substantially above 40 psig. Pressure is maintained via compressive hydrogen recycle in an amount such that the hydrogen/hydrocarbon mole ratio of the mixed feed to the dehydrogenation zone is less than 15.0:1.0. Unusually high hourly space velocities (defined as volumes of hydrocarbons charged per hour, per volume of catalyst disposed in the reaction zone) are used, and are in the range of about 10.0 to about 40.0.

ADSORPTION-SEPARATION

In describing the linear mono-olefin adsorption-separation section of the present combination process, it is understood that the precise method by which the separation from unreacted normal paraffins, forms no essential feature of my invention. Recognized is the fact that the prior art, some of which has heretofore been delineated, whether published literature, or issued patents, abounds in a wide variety of zeolitic molecular sieve technology, and especially as applied to the adsorptive-separation of various hydrocarbon mixtures. In such prior art, the terms "zeolite", "crystalline aluminosilicate" and "molecular sieve" are employed synonymously to allude to various structures of crystalline alumina and silica having pores in which one or more components of a given hydrocarbon mixture are selectively sorbed and retained within the pores, while one or more other components are rejected. Zeolitic adsorbents fall into a variety of classifications, generally determined by pore size and structure, depending upon the character of the component to be retained as well as the character of those components to be rejected. Thus, molecular sieves having a pore diameter of about five angstrom units are widely utilized to separate normal paraffins (sorbed and retained) from isoparaffins (rejected). With respect to the separation of linear mono-olefins (sorbed and retained) from the unreacted normal paraffins (rejected), molecular sieves having a pore diameter in the range of about five to about fifteen angstrom units, depending upon the character of the charge stock, are suitably employed. Although the adsorption-separation may be effective using multiple fixed-bed zeolitic zones in swing-bed fashion, as illustrated in U.S. Pat. No. 2,920,037 (Cl. 208-310), issued Jan. 5, 1960, the more recent sophisticated simulated moving bed technique, as illustrated in U.S. Pat. No. 2,985,589, issued May 23, 1961, is preferred. These simulated moving bed processes utilize a multi-port rotary valve which may be of the type shown in U.S. Pat. No. 3,040,777 (Cl. 137-625.15), issued June 26, 1962.

With respect to the separation and recovery of mono-olefins having from 3 to about 20 carbon atoms per molecule, suitable adsorbents are the type X and type Y crystalline aluminosilicate zeolites. General details of the compositions and manufacturing techniques of these may be had upon reference to U.S. Pat. No. 2,822,244 (Cl. 252-455), issued Apr. 14, 1959, and U.S. Pat. No. 3,130,007 (Cl. 23-113), issued Apr. 21, 1964, respectively. These molecular sieve zeolites contain exchangeable cationic sites which, by way of ion-exchange, will be prepared to contain one or more metal cations from the metals of Groups I-A, I-B, II-B and II-A. These metals include beryllium, lithium, sodium, magnesium, potassium, calcium, rubidium, strontium, cesium, barium, gold, copper, silver, zinc and cadmium. Generally, cations from the metals of Groups I-A, I-B and II-A are preferred; the sodium form of either of type X, or type Y zeolite is especially preferred.

Both liquid-phase and vapor-phase adsorptions may be utilized in this section of the present process, with the former being preferred. Liquid phase requires somewhat lower temperature levels which enhance the selectivity of the zeolite with respect to the mono-olefins. Typical adsorption-separation conditions include temperatures of from about 100° F. to about 400° F. and pressures in the range of from atmospheric of about 500 psig. Suitable desorbents constitute readily separable materials, i.e. having a boiling range sufficiently different from that of the feed such that fractional distillation is feasible.

BRIEF DESCRIPTION OF DRAWING

Various embodiments of the combination process encompassed by my inventive concept are presented in the accompanying drawing. These are presented by way of a simplified schematic flow diagram in which miscellaneous appurtenances such as pumps and compressors, heaters and coolers, condensers, heat-exchangers and heat-recovery circuits, start-up lines, controls, valving and similar hardware have been omitted. These are not essential to an understanding of the process, and the utilization thereof, to modify the illustration, is well within the purview of one processing the requisite skill in the petroleum processing field of endeavor. Certainly the resulting modification will not be beyond the scope and spirit of the appended claims.

DETAILED DESCRIPTION OF DRAWING

In the illustrated embodiment, the charge stock, being kerosene boiling range normal paraffins having about 11 to about 18 carbon atoms per molecule, is introduced by way of line 1; in the event that the feed stream contains olefinic material, at least a portion thereof will be diverted through line 13 to be introduced into hydrotreating zone 10 through line 9. The feedstock is derived from the total kerosene fraction originally obtained as an atmospheric straight-run cut. Following concentration of those hydrocarbons in the indicated carbon number range, the normal paraffins are separately recovered via an adsorption-separation technique similar to that previously described. The normal paraffin feed stream is admixed with a substantially olefin-free hydrotreated effluent in line 2, the mixture continuing therethrough into dehydrogenation reaction zone 3.

Dehydrogenation is effected in contact with a catalytic composite of about 0.375% platinum, 0.15% rhodium, 0.6% lithium and 0.4% tin, by weight as the elemental metals, combined with a gamma-alumina carrier material. Operating conditions include a pressure of about 25 psig., a temperature of about 860° F., a hydrogen/hydrocarbon mole ratio of about 7.5:1.0 and a liquid hourly space velocity approximating 28. These conditions result in a conversion to linear mono-olefins of about 8.5%, by volume. Reaction zone effluent passes through line 4 into separation zone 5 at substantially the same temperature and pressure. A normally liquid phase, containing unreacted normal paraffins and the linear mono-olefins, is withdrawn via line 7 and introduced thereby into stripping column 15. A hydrogen-rich vaporous phase, containing olefinic material, is withdrawn through line 11; a portion of this vaporous phase is removed from the system through line 12 on pressure control, and the remainder continues through line 11 for introduction, via line 9, into hydrotreating zone 10.

Notwithstanding that the foregoing dehydrogenation conditions and catalyst are intentionally selected to preclude formation of material boiling below the initial boiling point of the feedstock, some such hydrocarbonaceous components will be absorbed in the liquid phase withdrawn from separation zone 5 by way of line 7. Therefore, this principally liquid phase is preferably introduced into a reboiled stripping column in order to remove light ends, by way of line 16, and to concentrate a liquid stream containing linear mono-olefins and unreacted feed components in line 6. This liquid stream is introduced into adsorption-separation zone 8.

Adsorption-separation zone 8 contains an adsorbent of sodium-form type Y zeolite in which the sodium has been cationically exchanged with about 3.7% by weight of silver. The zone functions at a pressure of about 100 psig. and a temperature approximating 275° F. Desired linear mono-olefinic product, substantially free from di-olefins, paraffins, aromatics and non-linear olefins, is withdrawn via conduit 14. The normal paraffinic raffinate, containing a relatively minor quantity of olefinic material, is removed via line 9 and introduced into hydrotreating zone 10, in admixture with the hydrogen-rich vaporous phase from line 11. Hydrotreating zone 10 is maintained at a pressure of about 30 psig. Other conditions include a liquid hourly space velocity of about 5.0 and a temperature of about 450° F. The catalytic composite contains about 0.375% by weight of palladium and about 0.12% by weight of iridium. At these conditions, and in contact with the indicated catalyst, cracking reactions are minimized and the hydrotreated product effluent in line 2 is virtually void of olefinic material.

The foregoing specification, particularly when read in conjunction with the accompanying drawing, clearly illustrates the method by which the present combination process is effected.

I claim as my invention:

1. In a process for dehydrogenating a hydrocarbon charge stock, consisting essentially of normal paraffins having from about 3 to about 20 carbon atoms per molecule to form linear mono-olefins the sequential steps of:
    (a) reacting said charge stock in the presence of hydrogen, in a dehydrogenation reaction zone, at dehydrogenation conditions selected to convert paraffinic hydrocarbons to linear mono-olefinic hydrocarbons;
    (b) separating the resulting dehydrogenation zone effluent, in a first separation zone, at separating conditions to provide (1) a hydrogen-rich, principally vaporous phase containing olefinic hydrocarbons and, (2) a second phase containing linear mono-olefinic hydrocarbons and unreacted normal paraffins;
    (c) separating said second phase, in a second separation zone to (1) recover said linear mono-olefinic hydrocarbons, and (2) provide a normal paraffin concentrate containing olefinic hydrocarbons;
    (d) reacting at least a portion of said hydrogen-rich vaporous phase, in a hydrotreating zone, at hydrotreating conditions selected to saturate the olefinic hydrocarbons therein; and,
    (e) introducing the resulting substantially olefin-free effluent from said hydrotreating reaction zone into said dehydrogenation reaction zone.

2. The process of claim 1 further characterized in that said normal paraffin concentrate, containing olefinic hydrocarbons is introduced into said hydrotreating reaction zone.

3. The process of claim 1 further characterized in that at least a portion of said charge stock is introduced into said hydrotreating reaction zone.

4. The process of claim 1 further characterized in that said charge stock normal paraffins contain from 6 to about 10 carbon atoms per molecule.

5. The process of claim 1 further characterized in that said charge stock normal paraffins contain from 11 to about 18 carbon atoms per molecule.

6. The process of claim 1 further characterized in that said second separation zone in an adsorption-separation zone having disposed therein a zeolitic crystalline aluminosilicate molecular sieve adsorbent.

7. The process of claim 1 further characterized in that said dehydrogenation reaction zone has disposed therein a non-acid acting catalytic composite containing at least one Group VIII noble metal component.

8. The process of claim 1 further characterized in that said hydrotreating reaction zone has disposed therein a non-acid acting catalytic composite containing at least one Group VIII noble metal component.

9. The process of claim 6 further characterized in that said adsorbent is selected from the group consisting of type X and type Y structured zeolites.

10. The process of claim 9 further characterized in that said zeolite contains at least one metal cation from the metals of Groups I-A, II-A and I-B.

* * * * *